(12) United States Patent
Nousiainen et al.

(10) Patent No.: US 10,327,702 B2
(45) Date of Patent: Jun. 25, 2019

(54) BIOMETRIC MONITOR STRAP

(71) Applicant: PulseOn Oy, Espoo (FI)

(72) Inventors: Jari Nousiainen, Espoo (FI); Jarkko Saunamäki, Vantaa (FI); Eric Lam, Kwai Chung (HK)

(73) Assignee: PULSEON OY, Espoo (FI)

( * ) Notice: Subject to any disclaimer, the term of this patent is extended or adjusted under 35 U.S.C. 154(b) by 0 days.

(21) Appl. No.: 15/313,635

(22) PCT Filed: Feb. 27, 2015

(86) PCT No.: PCT/FI2015/050118
§ 371 (c)(1),
(2) Date: Nov. 23, 2016

(87) PCT Pub. No.: WO2015/181438
PCT Pub. Date: Dec. 3, 2015

(65) Prior Publication Data
US 2017/0202514 A1   Jul. 20, 2017

(30) Foreign Application Priority Data

May 30, 2014   (FI) ..................................... 20145499

(51) Int. Cl.
*A61B 5/024* (2006.01)
*A61B 5/00* (2006.01)
(Continued)

(52) U.S. Cl.
CPC .............. *A61B 5/6831* (2013.01); *A44C 5/14* (2013.01); *A61B 5/02055* (2013.01);
(Continued)

(58) Field of Classification Search
CPC ..... A61B 5/681; A61B 5/6824; A61B 5/6831; A61B 5/6801; A61B 5/6802;
(Continued)

(56) References Cited

U.S. PATENT DOCUMENTS 3,270,928 A * 9/1966 Brunet ..................... A44C 5/02
224/164
4,785,982 A * 11/1988 Iwamura .................. A44C 5/14
224/164
(Continued)

FOREIGN PATENT DOCUMENTS

EP   0660204 A1   6/1995
EP   2007273 B1   12/2008
(Continued)

OTHER PUBLICATIONS

Nordstrom Watch Case Size Guide. Nordstrom, Aug. 18, 2013, i.nordstromimage.com/images/default/shop/image/shops/watches/2013/0819/08.19.13_Watch_Size_Guide_54150.pdf.*
(Continued)

*Primary Examiner* — Niketa I Patel
*Assistant Examiner* — Nathan A Baldwin
(74) *Attorney, Agent, or Firm* — Ziegler IP Law Group, LLC

(57) ABSTRACT

The present application provides a portable biometric monitor (10) comprising a biometric sensor, wherein the housing of said portable biometric monitor is connected to a strap for attaching the portable biometric monitor to a user, the strap comprising a first end and a second end, wherein the strap comprises spacer elements (12, 13, 14, 15) having a first end and a second end, the strap being connected from its two sides at the first end and from its two sides at the second end to two sides at the first end of the housing and to two sides at the second end of the housing via pivots (16, 17, 18, 19) connected to said spacer elements to allow pivoted movement of the housing, wherein the distance of the pivot locations between the first end of the housing and the second end of the housing is in the range of 10-30 mm.

23 Claims, 11 Drawing Sheets

(51) Int. Cl.
    *A44C 5/14*     (2006.01)
    *A61B 5/0205*     (2006.01)
    *A61B 5/0404*     (2006.01)
    *A61B 5/0488*     (2006.01)
    *A61B 7/04*     (2006.01)
    *A61B 8/00*     (2006.01)
    *A61B 5/053*     (2006.01)

(52) U.S. Cl.
    CPC ...... *A61B 5/02416* (2013.01); *A61B 5/02438* (2013.01); *A61B 5/0404* (2013.01); *A61B 5/0488* (2013.01); *A61B 5/6843* (2013.01); *A61B 7/04* (2013.01); *A61B 8/4227* (2013.01); *A61B 5/0533* (2013.01); *A61B 5/681* (2013.01); *A61B 5/6823* (2013.01)

(58) Field of Classification Search
    CPC ....... A61B 5/6828; A44C 5/0023; A44C 5/14; A44C 5/16; Y10T 24/4718; Y10T 24/4782
    See application file for complete search history.

(56) References Cited

U.S. PATENT DOCUMENTS

| | | | | |
|---|---|---|---|---|
| 5,159,713 | A * | 10/1992 | Gaskill | G04G 21/04 340/7.53 |
| 5,215,235 | A | 6/1993 | Maekawa et al. | |
| 5,363,351 | A | 11/1994 | Carney | |
| 5,577,007 | A * | 11/1996 | Houlihan | A44C 5/14 224/164 |
| 6,130,862 | A * | 10/2000 | Upton | G04B 37/1486 368/282 |
| 8,668,696 | B2 * | 3/2014 | Foerster | A61B 17/82 24/171 |
| 2002/0151775 | A1 | 10/2002 | Kondo | |
| 2005/0115122 | A1 * | 6/2005 | Fishman | A01K 11/00 40/304 |
| 2009/0168612 | A1 | 7/2009 | Robin et al. | |
| 2009/0312655 | A1 * | 12/2009 | Lo | A61B 5/02438 600/503 |
| 2012/0304784 | A1 | 12/2012 | Isaacson et al. | |
| 2013/0088942 | A1 * | 4/2013 | Perko | G04R 60/10 368/278 |
| 2013/0120106 | A1 | 5/2013 | Cauwels et al. | |
| 2014/0257049 | A1 * | 9/2014 | Soundarapandian | A61B 5/681 600/301 |
| 2015/0189956 | A1 * | 7/2015 | Rivera | A44C 5/0007 224/152 |

FOREIGN PATENT DOCUMENTS

| | | |
|---|---|---|
| GB | 361821 A | 11/1931 |
| GB | 2482222 A | 1/2012 |

OTHER PUBLICATIONS

International Preliminary Report on Patentability, Application No. PCT/FI2015/050118, dated May 16, 2016, 18 pages.
International Search Report, Application No. PCT/FI2015/050118, dated Jun. 2, 2015, 4 pages.
Extended European Search Report, Application No. 15800688.2-1657/3148363 PCT/FI2015050118, dated Nov. 15, 2017, 8 pages.

* cited by examiner

BIOMETRIC MONITOR STRAP

CROSS-REFERENCE TO RELATED APPLICATIONS

This application is a National Stage of PCT/FI2015/050118 which claims Priority to Finnish Application Number 20145499, the disclosures of which are incorporated herein by reference in their entireties.

FIELD OF THE APPLICATION

The present application relates to a portable biometric monitor strap and to a portable biometric monitor comprising said strap. More particularly the present application relates to a wearable biometric monitor, such as a heart rate monitor for attaching to a wrist of a user.

BACKGROUND

Physiological data can be measured from a user by using portable biometric monitors, which may be attached to the user, for example to the wrist, forearm, or arm of the user. The physiological data may include for example heart rate. Traditional monitors usually contain a separate sensor, which is attached for example to the user's chest with a strap, and which communicates wirelessly with the wrist device. The use of separate sensors complicates the use of a portable biometric monitor, and therefore there is a need to develop solutions embedded to the wrist-attached or other extremity attached device.

One way for measuring the heart rate is using optical measurement. The optical heart rate measurement is based on the fact that light is emitted by a light source towards body tissue and at least one detector is configured to detect the intensity of reflected light after propagation through the body tissue.

In such measurement a photoplethysmogram (PPG) is obtained. It is an optically obtained plethysmogram, a volumetric measurement of an organ. A PPG is often obtained by using a pulse oximeter which illuminates the skin and measures changes in light absorption. With each cardiac cycle the heart pumps blood to the periphery. Even though this pressure pulse is somewhat damped by the time it reaches the skin, it is enough to distend the arteries and arterioles in the subcutaneous tissue. If the pulse oximeter is attached without compressing the skin, a pressure pulse can also be seen from the venous plexus, as a small secondary peak.

The change in volume caused by the pressure pulse may be detected by illuminating the skin with the light from a light-emitting diode (LED) and then measuring the amount of light either transmitted or reflected to a photodiode.

Each cardiac cycle appears as a downward peak in the photodiode. Because blood flow to the skin can be modulated by multiple other physiological systems, the PPG can also be used to monitor breathing, hypovolemia, and other circulatory conditions. Additionally, the shape of the PPG waveform differs from subject to subject, and varies with the location and manner in which the pulse oximeter is attached.

There are several challenges when measuring pulse optically. The optical measurement is based on light absorption changes caused by blood flow in a lighted area. If the shape of the lighted area changes during the measurement, for example, due to movement of the pulse measuring device, the measurement is disturbed. Thus, for example, movements of a hand and of the user cause errors to the measurement in many ways.

In order to avoid problems in the measurement of biometric monitors, especially in optical measurements, the device needs to be as stable as possible in relation to skin and needs to minimize mechanical changes in tissue area during movement. This is especially important during activities, such as sports-related activities and workouts, and when the biometric monitoring device is used as an athletic performance or fitness monitor.

The wrists of different users may vary in size ranging in perimeter for example from 12 cm to over 20 cm. This makes it very challenging to optimize the contact of the portable biometric monitor for use with all or most of the users, as the devices are usually produced in one size only.

There are many ways to address the above problems. One solution is to tighten a strap of the measuring device. The problem, however, is that a user may tighten the strap too much, which in turn is uncomfortable and prevents blood flow in tissue. In turn, too loose tightening of the strap allows the portable measuring device to move too much in relation, for example, to a wrist and body tissue. Further, too complicated tightening and setting procedure makes the device less convenient to use.

SUMMARY

One embodiment provides a portable biometric monitor comprising a biometric sensor, wherein the housing of said portable biometric monitor is connected to a strap for attaching the portable biometric monitor to a user, the strap comprising a first end and a second end, wherein the strap comprises spacer elements having a first end and a second end, the strap being connected from its two sides at the first end and from its two sides at the second end to two sides at the first end of the housing and to two sides at the second end of the housing via pivots connected to said spacer elements to allow pivoted movement of the housing, wherein the distance of the pivot locations between the first end of the housing and the second end of the housing is in the range of 10-30 mm.

The aspects of the invention are characterized in the independent claim. Various embodiments are disclosed in the dependent claims. The features recited in dependent claims and in the description are mutually freely combinable unless otherwise explicitly stated.

The construction of the portable biometric monitor enables efficient packing of the electronics inside the housing. As the pivots do not have axles reaching through the whole casing of the device, there is more room for the electronics, sensors, displays, mechanics and the like. This has an effect of enabling more compact design on the device, which helps for example controlling the contact of the device with the user and making the wearing more comfortable due to small size. With a compact device the attachment of the strap to the device itself may be implemented in a way which enables the attachment points being close to each other.

As the strap is connected to the body of the monitor with movable spacer elements, which are connected to the body via pivots, which are close to each other, the movement of the user, for example the movement of the wrist of the user, has less disturbance to the contact of the device with the user.

The pivoted structure prevents the monitor as a whole from pivoting up at one end when the user's wrist moves or turns, or if the strap tends to rotate or move in the wrist, as is the case with conventional rigid structures. The pivoted structure provides an effect of adapting the wrist strap to the rotating movements and shapes of different types of wrists. The mechanical behavior of the structure is made short, i.e. the effective length of the biometric monitor attached to the strap is shorter than the actual length of the monitor. As there are different types of wrists having different dimensions and angles, the pivoted structure may turn even about 90 degrees independently at each end, thus adapting to the contour of the user's wrist. This minimizes the leverage effect directed to the strap attachment caused by the movements of the wrist. The force required for lifting the monitor is maximized and simultaneously the force required for maintaining the position of the monitor is minimized.

This provides an effect of enhancing the contact of the device and the sensor with the skin of the user and maintaining an unchanged position of the monitor on the wrist. If the pivots were more far away from each other, said movements would move the device body in a way which would break the contact of the device with the skin. The distance of the pivot locations between the first end of the housing and the second end of the housing used in the embodiments were found to be optimal for different sizes of wrists thereby providing an efficient arrangement useful for practically all users.

The feature of pivoted movement of the housing enables wrist movements without disturbing the contact of the device with the skin. This provides an effect of enhancing the contact of the device and the sensor with the skin of the user.

The design of the strap attachment to the body of the monitor has an effect of reducing the pressure of the device against the skin, and at the same time enhancing the stability of the device on the skin. The enhanced stability and the enhanced contact provide an effect of reducing the changes in the pressure, angle and movement of the device, which enhances the measuring accuracy, especially with optical sensors. Also this provides enhanced convenience of use of the device as there is no need to overtighten the strap. If a stretchable strap is used the design enables immediate stability and contact of the device with the user's skin already without further adjustment of the strap. This provides an effect of allowing the slipping of the device to a wrist and starting the use thereof immediately thus saving time and allowing convenient use.

The feature that the pivot is non-movable at the housing side has an effect of providing a reliable and solid construction of the device. Such construction is also water-proof with no need for any further sealing. The pivot being made of metal also provides the same effects. Non-movable metallic pivots provide an effect of enhancing the contact in the grounding inside the housing and making it more reliable, for example when using spring-like grounding members touching the pivots. This is also beneficial during the assembly of the device.

The shape of the spacer elements provides an effect of keeping the strap side of the spacer elements close to the skin. The thickness of the strap side axle brings the level of the pivot center however slightly over the skin which further enhances the stability of the device.

The feature that the spacer elements and/or pivots are made of metal provides an effect of enabling smaller dimensions of the parts, such as thinner spacer elements, which further enable smaller dimensions and/or weight of the device. Also the mechanical durability and strength of the parts and the device are enhanced.

The effects provided by the attachment of the strap to the housing may also be affected by the overall tightness of the strap. This tightness may be controlled by the implementation of a buckle of the strap, the material of the strap and the mechanical indicator configured to indicate tightness of a strap described herein. By adjusting the tightness and maintaining the desired tightness enhanced stability of the device on the skin may be obtained.

The implementation of the buckle of the strap having an extension between the two portions of the strap entering and exiting the buckle prevents the strap from being moved through the window by friction when the flexible strap is extending and contracting due to human body movement provides an effect of maintaining the stability of the strap in use. Without the extension the two portions of the strap would be in close contact with each other and the friction between the portions would loosen or even tighten the strap due to the body movements, such as wrist movement.

BRIEF DESCRIPTION OF THE FIGURES

FIGS. 1A and 1B show two different orientations of the pivots and demonstrate the pivoted movement of the device.

FIG. 3A shows inner parts of the device related to the grounding, wherein

DETAILED DESCRIPTION

Biometrics refers to metrics related to human characteristics. Biometric identifiers are distinctive, measurable characteristics used to label and describe individuals. Biometric identifiers may comprise physiological data. The biometric monitor described herein is arranged to monitor or measure one or more of such biometric identifiers from an individual user, such as to detect, collect, save and/or process such information. The biometric monitor may be arranged to output one or more results from such one or more measurements.

One embodiment provides a portable biometric monitor 10 comprising a housing 20 having a first end 21 and a second end 22, and one or more processors, memory, one or more biometric sensors, and an interface operatively connected together. The biometric monitor may be a wearable monitor used as a sport or fitness monitor, health monitor or the like. The biometric sensor is located on the skin side or the user side of the monitor. This means the side of the casing which is in contact with the user skin during the use. This may also refer to the bottom of the monitor. In one example the portable biometric monitor 10 further comprises wireless radio technology, such as a transmitter and a receiver, operatively connected to the one or more processors, one or more biometric sensors, and/or the interface.

Figure 1A:
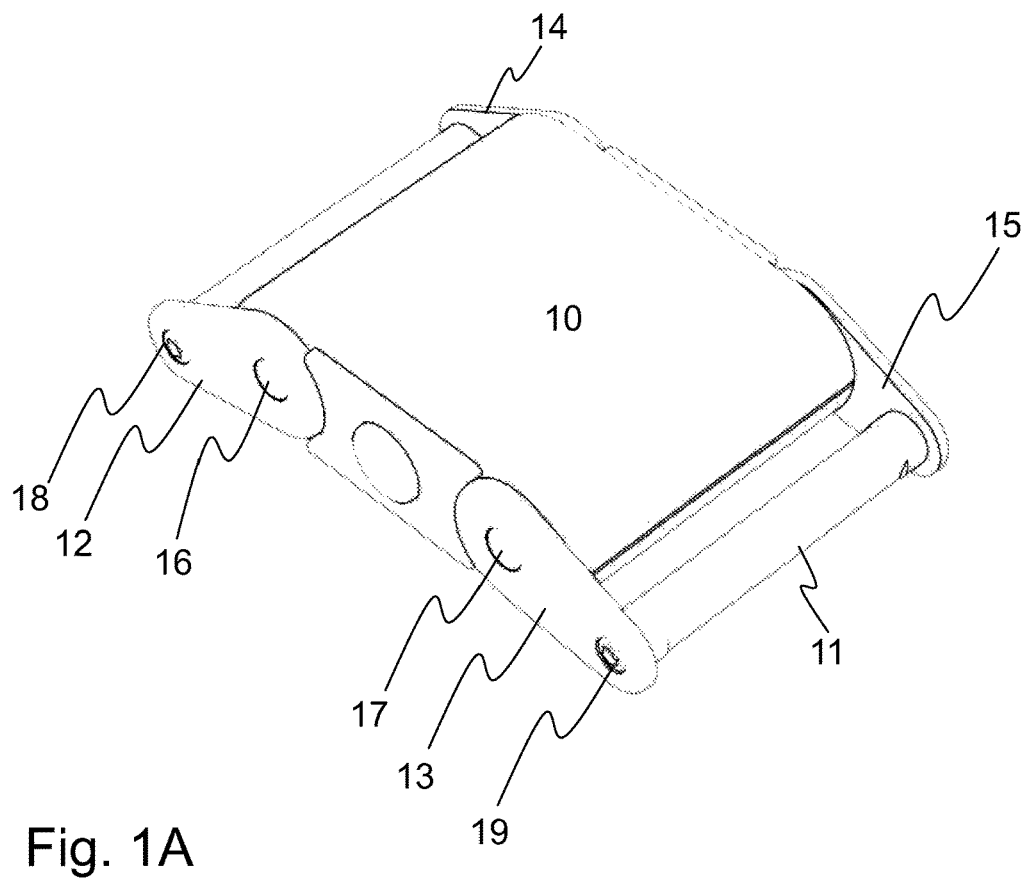
FIGS. 1A and 1B show the outer parts of the biometric monitor.
Figure 1B:
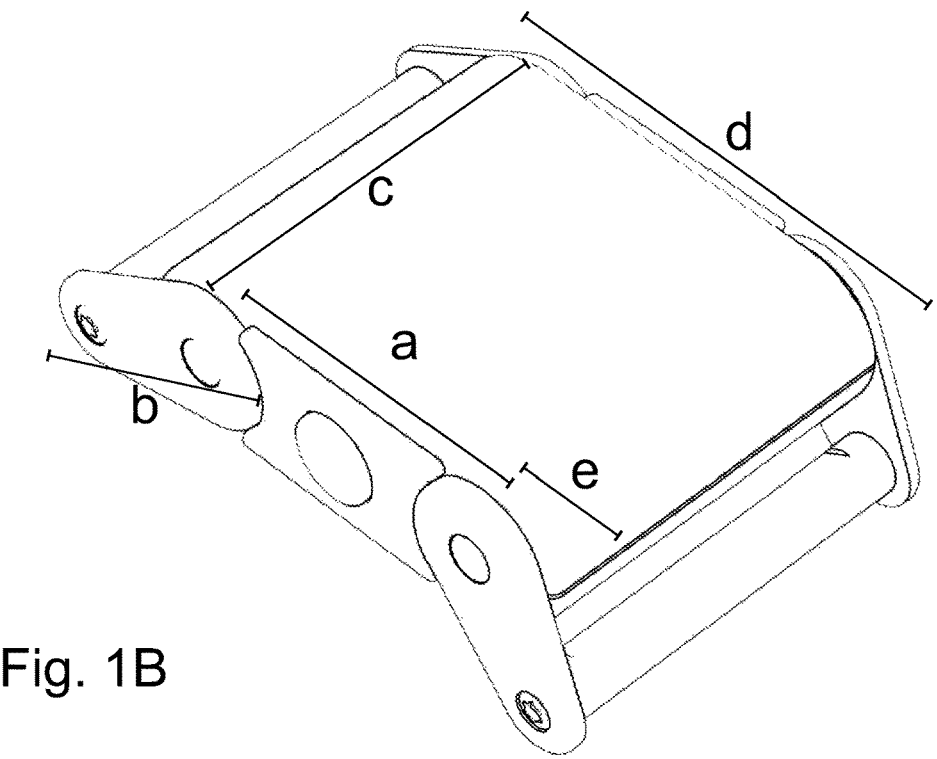

The main parts visible outside are shown in FIGS. 1A and 1B. The housing of said biometric monitor 10 may generally have a shape and the size of a wrist watch, for example it may be have a length d in the range of 20-60 mm, for example in the range of 25-40 mm. It may have a width c in the range of 15-40 mm, for example in the range of 25-35 mm, or in the range of 25-30 mm. The shape of the housing is generally substantially flat, having a thickness in the range of 3-15 mm, for example in the range of 5-10 mm, or in the range of 8-10 mm. In one example the housing is angular in shape, for example substantially square. The edges may be rounded. The housing may also have an oval or round shape, or a combination of the shapes mentioned herein. The first end 21 and the second 22 end may be defined according the direction of the housing when attached to the user or to the strap, especially in the case wherein the shape of the housing is substantially rounded. In one example the length of the housing is larger than the width thereof. The housing may also be called as a casing, a body or a frame of the biometric monitor. The housing may be made of metal, or it may have a body or frame made of metal. This enables mechanically reliable joints with the pivots or axles. Examples of metal include iron, steel, stainless steel, titanium, light alloys and the like. The housing may also be made of plastics or composite materials, such as reinforced plastic composites. Housing made of plastics or composite material may be used to provide products having decreased weight, to save in the manufacturing costs and to facilitate the manufacturing process. In such case the pivots may be anchored to the housing for example by using metal lockwashers inside the housing, and by using a connecting part 39 made of metal arranged to receive the pivots, usually arranged to receive two pivots at the same side of the monitor. The connecting part 39 is grounded via the pivots, and it also grounds the side plate 38.

The housing is connected to a wearable strap 40 for attaching the portable biometric monitor to a user, for example to a wrist of the user, the strap comprising a first end 41 and a second end 42. The strap may be continuous including only one strap part, or it may be discontinuous including at least two parts which may be connected by a buckle. In one example the strap contains two parts connected by a buckle, as shown in FIGS. 4A, 5A, 6A and 7A. The strap may have a width of substantially the width of the housing, or little less, such as 0.5-2 mm narrower than the width of the housing. The thickness of the strap may be in the range of 0.5-3 mm. In one example the strap is made of stretchable or elastic material, such as canvas, rubber, silicone or combinations thereof. In one example the strap is made of non-stretchable material, such as plastics, leather, metal, or combinations thereof. Examples of metal include steel, stainless steel, titanium, light alloys and the like. The surface of the strap material, for example rubber or silicone, may also provide friction, which may enhance the contact with the user and prevent the strap from spinning for example around the user's wrist. This effect together with the pivoted structure helps maintaining the contact of the biometric sensor with the user.

The strap 40 includes spacer elements 12, 13, 14, 15 having a first end 24 and a second end 25, meaning that the strap 40 is connected to said spacer elements 12, 13, 14, 15. The spacer elements 12, 13, 14, 15 may also be called spacers, linkers, spacing parts, link parts, linking parts, link elements or the like. In one example said spacer elements are thin or flat strip-like parts having a thickness in the range of 0.5-3 mm, for example in the range of 0.7-2 mm, or in the range of 0.7-1.5 mm. In one example said spacer element has a thickness of about 1 mm. In one embodiment the spacer elements have a length bin the range of 10-20 mm, for example in the range of 15-18 mm. The spacer elements 12, 13, 14, 15 are configured to receive a pivot 16, 17 at the first end 24 and a pivot 18, 19 at a second end 25, or the spacer elements 12, 13, 14, 15 have a hole for the pivots 16, 17 at the first end 24 and a hole for the pivots 18, 19 at the second end 25. In the final biometric monitor construction the spacer elements are connected to said pivots, i.e. the spacer elements include said pivots. In one embodiment the spacer element is not fixed to a pivot, i.e. the spacer element is movable in relation to said pivot, or it is rotatable around said pivot. The pivots may be fixed to the housing side of the biometric monitor. The FIGS. 1A and 1B demonstrate the movement of the pivots.

The strap is connected from its two sides at the first ends 41 and from its two sides at the second ends 42 to two sides at the first end 21 of the housing 20 and to two sides at the second end 22 of the housing 20 via said spacer elements 12, 13, 14, 15.

The spacer elements 12, 13, 14, 15 are connected to the housing 20 via pivots 16, 17 at the first end 24 of said spacer elements 12, 13, 14, 15 and to the strap 40 via pivots 18, 19 or an axle at the second end 25 of said spacer elements 12, 13, 14, 15 to allow pivoted movement of the housing 20 and/or the strap 40, especially free pivoted movement. The distance a of the pivot locations between the first end of the housing and the second end of the housing, on the same side, may be in the range of 10-30 mm, for example in the range of 20-30 mm. In one embodiment the distance a of the pivot locations between the first end of the housing and the second end of the housing is in the range of 20-25 mm, or more precisely in the range of 21-23 mm, for example about 22 mm. This range is suitable especially for wrist devices with relatively small size.

However, in some cases the distance a of the pivot locations between the first end of the housing and the second end of the housing, on the same side, may be even more, such as in the range of 10-50 mm, for example 20-50 mm, 10-40 mm, 20-40 mm, 31-50 mm or 40-50 mm. Examples of such distances include about 30 mm, 35 mm, 40 mm, 45 mm and 50 mm. The longer distances may be used with larger devices, which also may be applied to other parts of the user's body.

The spacer elements may form an angle of about 110 degrees with the housing, for example about 100 degrees, or even about 90 degrees. The structure allows for independent angles at both sides of the housing. In the example of FIG. 1B the contour of the side plate 38 is arranged to limit the angle to about 100 degrees.

The ends of said flat spacer elements may be rounded and the other end may be narrower than the other end. For example the first end 24 is connected to the housing 20 and may have substantially the same width as the thickness of the housing, for example in the range of 8-10 mm at the level of the pivot center. The second end 25 is connected to the strap 40 and it may have a smaller width than the first end, for example in the range of 4-7 mm at the level of the pivot center. This width is close to the diameter of the axle 11 attached to the strap 40, the diameter of the axle 11 being for example in the range of 3-5 mm. The pivots 18, 19 may be connected to the axle 11, for example the pivots may be screws which have been screwed to a hole in the axle 11, or the pivots may form a part of the axle. The axle 11 may be made of metal, or it may be made of plastics. In the described case the general tapered shape of the spacer element resembles a drop or a "dog ear". This shape provides maximum contact of the spacer element with the user at any position of the spacer element, which provides enhanced mechanical support and electrical contact, such as grounding of the device.

On the strap side there may be only one axle 11 reaching from one side to the other side. Usually this axle 11 is inside a strap loop 48. The relatively smaller width of the second end 25 of the spacer element 12, 13, 14, 15 enables the connection to the strap 40 being relatively close to the skin of the user. This has an effect of enhancing the stability of the biometric monitor. However, the diameter of this axis 11 together with the thickness of the strap places the center of the axis 11 slightly over the skin surface, for example by 2-5 mm. This distance was found to further stabilize the construction during use.

In one embodiment the pivots are connected to the housing at locations which are at a distance e in the range of 3-10 mm from the ends 21, 22 of the housing 20, for example in the range of 4-8 mm. In one example this distance is about 5 mm.

In one embodiment the pivots are connected to the housing at locations which are at a distance e in the range of ¼-1/10 of the length d of the housing 20 from the ends 21, 22 of the housing 20, for example at a distance in the range of ⅕-⅐.

Figure 3A:
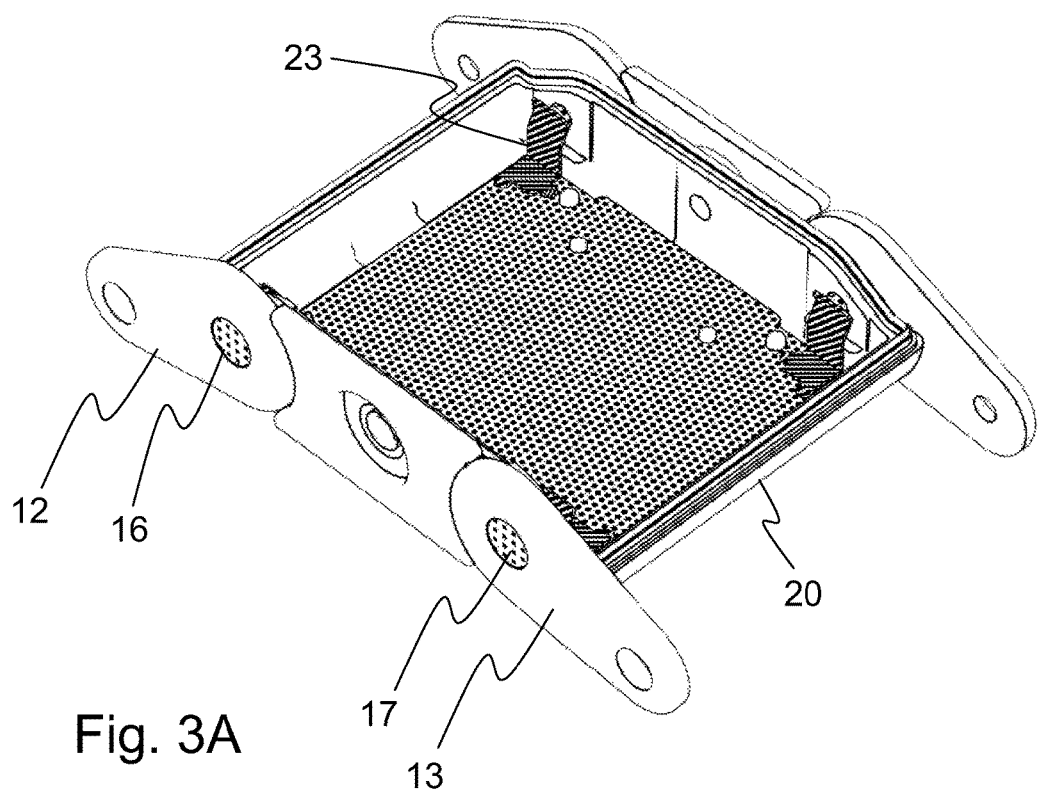
Figure 3B:
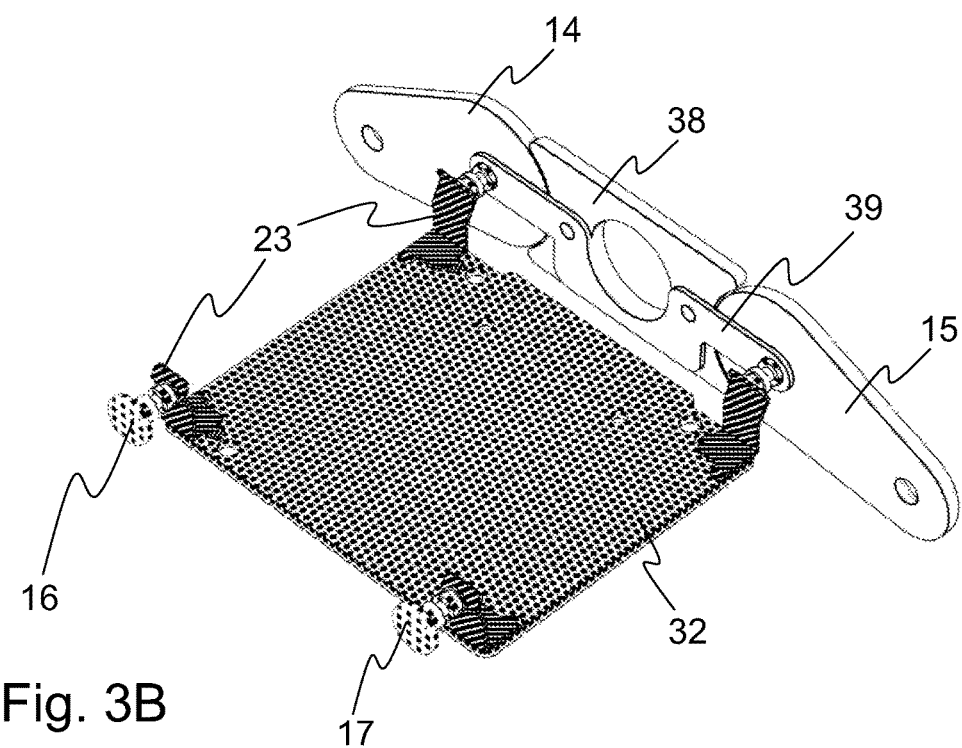
FIG. 3B shows the same view without the spacer elements and other parts on the other side

The pivots comprise axles or the pivots may be also called axles. In one embodiment the pivots on the two sides of the housing are separate pivots not penetrating through the whole housing. Separate pivots enable independent movements of each spacer element, i.e. the pivots at the different sides of the housing are not interconnected and therefore the movement thereof and the spacer elements are not synchronized. The pivots and/or the spacer elements are therefore independently movable. Each of the spacer elements is capable of forming an angle with the housing independently, i.e. each of the spacer element may form a different angle with the housing. Especially the spacer elements at the different ends of the housing may form independent angles with the housing. The pivot may protrude inside the housing only to the level of the housing itself, or it may protrude further only by 1-2 mm. The total length of said pivot may be in the range of 2-5 mm, for example about 3 mm. FIGS. 3A and 3B show examples of the structures and the lengths of the pivots. In FIG. 3A it can be seen that the pivots protrude slightly inside the casing to allow contact with the grounding elements 23.

The pivots are preferably not connected to any further mechanisms, for example inside the housing. This means that the pivots and/or the spacer elements are freely movable. No arrangements are connected to the pivots or to the spacer elements which may slow down the movement thereof, such as arrangements for collecting kinetic energy mediated by the spacer elements. Said separate, independent and freely movable structures of the pivots and/or the spacer elements can be seen for example in the FIGS. 2A, 2B, 3A and 3B.

The short lengths of the pivots provide more space inside the casing as there are no axles protruding through the housing. However, as the pivots are relatively short, they are preferably made of metal to maintain the mechanical strength and rigidity. Also, as the biometric monitor usually utilized wireless radio technology, the grounding of the electronics is important. It is preferred that the grounding is conducted to the skin of the user. This may be implemented by using conductive material in both the pivots and the spacer elements, such as metal. The spacer elements are in contact with the user during the use of the device.

In one embodiment the pivots are made of metal. In one embodiment the spacer elements are made of metal. In one embodiment both the pivots and the spacer elements are made of metal. Examples of metal include steel, stainless steel, titanium, light alloys and the like.

In one embodiment the pivot is non-movable at the housing side. This may also be called a fixed axle. Preferably this is implemented in a water-proof way. When a metal pivot or axle is used the mechanical strength of the assembly is high. A water resistant joint may be obtained without using any separate seals. In one embodiment the pivots are movable at the housing side. There may be a lockwasher inside the housing to keep the pivots attached to the housing. In general the spacer elements are freely and independently movable. In one example the housing is water-resistant, or the biometric monitor is water-resistant. Also the term "water proof" may be used interchangeably. In such case seals, such as rubber seals or similar elastic seals, may or may not be used. In one example there are no seals in the joints between the pivots and the casing, but other seals may exist in the device.

In one embodiment the strap is a wrist strap. Other examples of the straps include forearm straps, ankle straps, forehead straps, tights straps, leg straps, arm straps and neck straps. However, the dimensions used in the embodiments herein are optimized for wrist straps for different wrist sizes.

In one embodiment the biometric sensor is an optical sensor. Other examples of biometric sensors include a temperature sensor, a potential sensor, a sound or an ultrasound sensor, an impedance sensor, a galvanic skin response sensor (GSR), an EKG sensor, an EMG sensor, and a wavelength sensor. The biometric monitor may contain one or more biometric sensor(s), for example two, three or four sensors. Also other sensors may be included, such as a GPS sensor, a magnetometer, or a motion detector, for example inertia, gyro or accelerometer. Usually the biometric sensor is located on the skin side or the user side of the monitor. In one example the portable biometric monitor contains an optical sensor and at least one sensor selected from a temperature sensor, a potential sensor, a sound or an ultrasound sensor, an impedance sensor, a galvanic skin response sensor (GSR), an EKG sensor, an EMG sensor, and a wavelength sensor. These sensors are directed towards the skin of the user, and they are arranged to detect one or more features from the user. Therefore such sensors are sensitive to the contact of the device with the user so the stability and other advantages provided by the strap attachment are especially advantageous for these sensor types. In one example the portable biometric monitor comprises an optical sensor and a galvanic skin response sensor. In one example the portable biometric monitor comprises an optical sensor and an impedance sensor.

Examples of possible physiological parameters to be monitored with the one or more biometric sensors in addition to heart rate include body temperature, blood pressure, blood flow, skin conductivity, tissue impedance, heart rate variability, motion, sleep, stress, fitness level, recovery level, effect of a workout routine on health, and caloric expenditure.

In one embodiment the portable biometric monitor is a heart rate monitor, or a pulse monitor. In one embodiment the portable biometric monitor is a heart rate monitor comprising an optical sensor, or an optical detector. The optical heart rate monitoring may be based on light scattering monitoring. In general an optical sensor includes one or more light or illumination sources for emitting light and one or more light or illumination detectors for detecting the light scattered or reflected from the user's body. Examples of the light sources include LED, laser and the like. Examples of the light detectors include photodiodes, phototransistors and the like. In one example the optical sensor comprises a light source and a light detector. In one example the optical sensor comprises two light sources and a light detector between the light sources, preferably all in a line. In one example the optical sensor comprises three light sources and two light detectors between the light sources, preferably all in a line. The light source(s) may emit light at one or more wavelength(s) or wavelength ranges. The light detector(s) may detect light at one or more wavelength(s) or wavelength ranges. Examples of such wavelength ranges include green spectrum, blue spectrum, red spectrum, and infrared spectrum. The light source(s) or the light detector(s) may further have a filter for filtering out undesired wavelengths. Examples of specific light sources having a specific wavelength range include green LED, blue LED, red LED, infra-red (IR) LED, near infra-red LED and combinations thereof. In general green light is suitable for the measurement of superficial blood flow in skin. Light with wavelengths between 500 and 600 nm (the green-yellow region of the visible spectrum) exhibits the largest modulation depth with pulsatile blood absorption. IR or near-IR wavelengths may be better for measurement of deep-tissue blood flow, such as blood flow in muscles. In one example the light source is an infra-red (IR) LED or a near infra-red LED.

In one example the light source is a green LED. A green LED has much greater absorptivity for both oxyhaemoglobin and deoxyhaemoglobin compared to for example infrared light. Therefore, the change in reflected green light is greater than that in reflected infrared light when blood pulses through the skin, resulting in a better signal-to-noise ratio for the green light source. Infrared light may be used also to measure skin's moisture content on the absorption of infrared light by the dermis, or for other purposes.

Figure 2A:
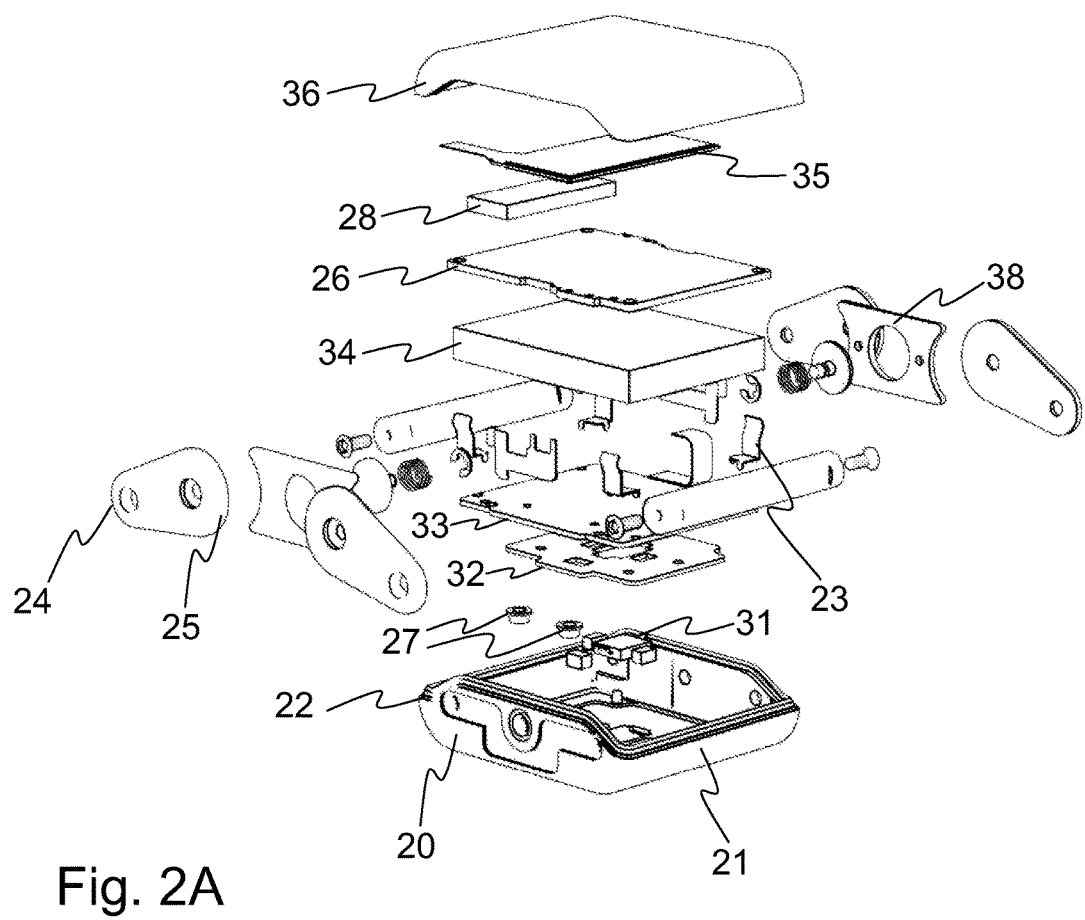
FIG. 2A shows an exploded view of the biometric monitor.
Figure 2B:
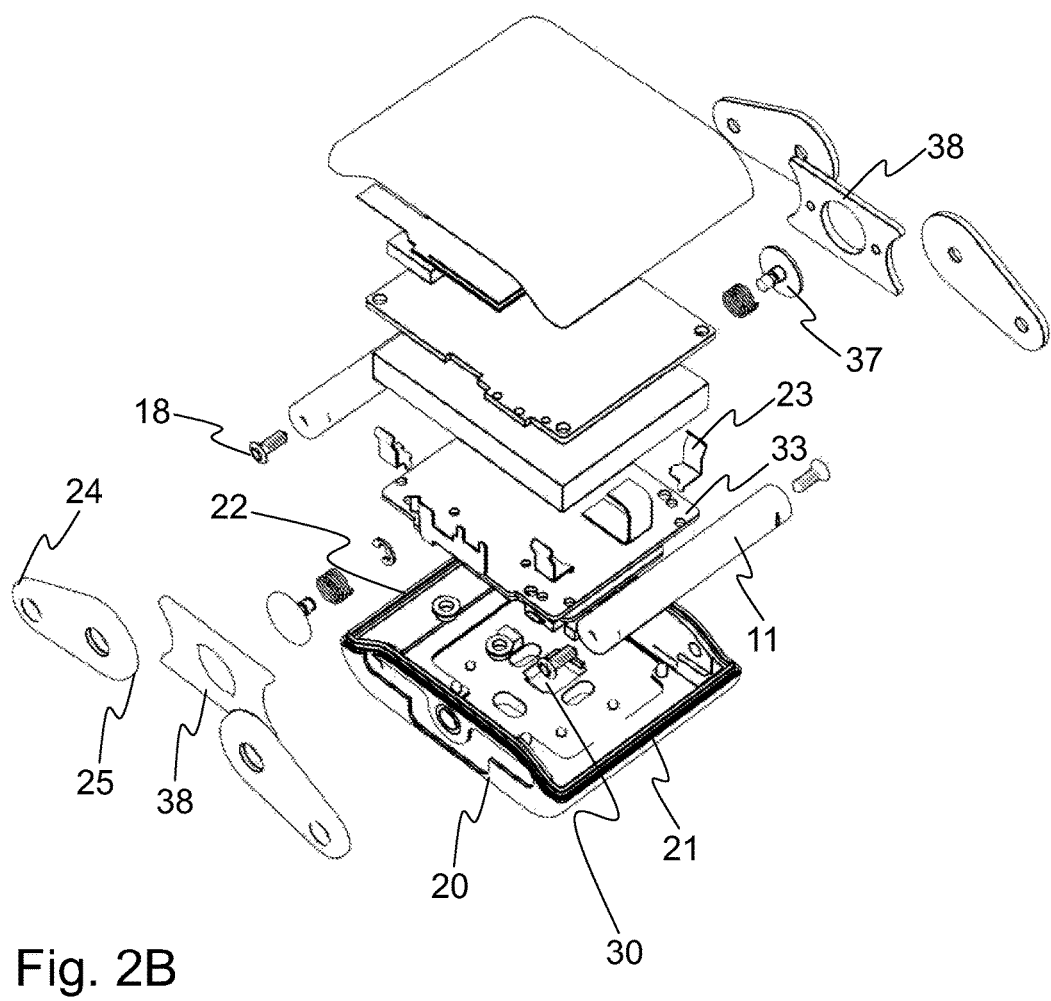
FIG. 2B shows the view from a different angle

The optical sensor is mounted at the bottom of the monitor body, on the skin side of the user. The optical sensor may form a protrusion of about 0.5-2 mm from the bottom of the monitor for anchoring the sensor to the skin, generally the protrusion having curved sides. Usually this is on the opposite side of the monitor body in relation to the display. In one example the optical sensor does not form a protrusion, i.e. the bottom of the monitor is flat. FIG. 2B illustrates holes for the optical sensor in the bottom of the housing 20. The housing may contain one hole or aperture for the optical sensor as a whole, or separate holes or apertures for the light source(s) and for the light detector(s). In one example the device further includes a gasket or a sealing plate 32 which prevents leakage of the light inside the device.

In one example a portable biometric device having an optical sensor includes at least one light source and at least one light detector installed onto a circuit board, a casing having at least one aperture for said at least one light source and at least one aperture for said at least one light detector, and a sealing plate between said casing and said circuit board, said sealing plate having at least one aperture for said at least one light source and at least one aperture for said at least one light detector, wherein each of said at least one light source and at least one light detector are optically isolated from each other inside said casing. The feature that the at least one light detector and the at least one light source are optically isolated from each other inside the casing provides an effect of preventing leakage of light inside the device between the light source and the light detector. The light detected by the light detector comes only from outside the device. This enhances the sensitivity and the accuracy of the measurement providing better signal to noise ratio and signal to DC values.

"Optically isolated" as used herein refers to an arrangement wherein each of at least one light sources and each of at least one light detectors are arranged in separate optically isolated compartments, which are not optically connected. This means that the leakage of light from one compartment to another inside the casing has been prevented by using suitable isolating material between the compartments, such as the gasket or the sealing plate described herein. Said sealing plate has at least corresponding apertures for the optical components as are present in the casing. The only light path from such an optically isolated compartment preferably leads outside the casing through an aperture in the casing, which aperture is arranged to be positioned against the skin of the user when the biometric monitor is in use. In the case of more than one light sources the casing may contain more than one apertures.

In one embodiment the portable biometric device comprises at least one lens optically connected with said at least one light source and at least one lens optically connected with said at least one light detector. "Optically connected" as used herein refers to an arrangement wherein a lens and a light source, or a lens and a light detector are positioned so that the light emitted by the light source exits through the corresponding lens, or a light detected by the light detector enters through the corresponding lens. In practice this means that the corresponding lens is placed on top of the light source or the light detector, either directly or with a gap between, and with adhesive or without adhesive. The lens refers to a transparent piece, which may be for example made of plastics or glass. The lens may or may not refract light. The lenses protect the optical components inside the casing preventing water and/or dust entering the casing. The lenses may be arranged to refract the emitted light reflected from the user's skin so that it will be detected in optimal angle and intensity. In one example the lens is converging. In one example the surface of a lens is flat i.e. not refracting. In one example the lenses are placed in a corresponding aperture in the casing which is tight enough to retain the lens. Adhesive may be used to enhance the adhesion. In one example the lenses are placed in a corresponding aperture in the casing from inside the casing and the inner side of a lens is wider than the outer side of the lens so that the outer side fits the aperture and the wider inner side prevents the lens from slipping through the aperture More precisely the optical heart rate monitoring is implemented by irradiating the skin of the user with visible or infrared light generated by said light source. The light source is generally arranged in close contact with the skin of the user. A light detector is arranged also in close contact with the skin in a nearby location and it is arranged to detect and measure the light resulting from reflection, absorption and/or scattering by the skin. The variations in said detected and measured values allow the measurement of the flow of oxy- and deoxyhemoglobin and the expansion of blood vessels. A photoplethysmogram (PPG) may be obtained. This enables for example oxymetric and pulsometric measurements, which may be further used to define the heart rate of the user.

In addition to heart rate, an optical sensor may be configured to monitor the user's respiration, heart rate variability, oxygen saturation ($SpO_2$), blood volume, blood glucose, skin moisture and/or skin pigmentation level.

In one embodiment the portable biometric monitor, or the electronics thereof, is grounded to the metallic pivot from inside the housing with grounding elements. This is necessary especially in biometric monitor using radio frequency communication to transfer data or otherwise exchange information wirelessly with another device or entity, and/or if such biometric monitor uses radiofrequency sensing such as GPS for location detection. In one embodiment the portable biometric monitor is grounded to the metallic pivot via a spring member 23 as the grounding element, as illustrated in FIGS. 3A and 3B. The spring member 23 protrudes from the electronics module to a location of the metallic pivot or axle inside the casing and touches the pivot or axle to obtain an electrical contact with it. The spring force directed to the pivot maintains the electrical contact. No soldering or the like is required to establish a reliable contact, which saves time and costs during the assembly of the device, or in case when disassembly is required, for example during a service. However, the spring does not prevent the free movement of the pivots. In one example the grounding elements are integral parts of a metallic bottom plate 33, which is located between the electronics and the biometric sensor. In one example the grounding elements are separate elements, which are connected to a larger grounding part, such as a metallic bottom plate 33. An example of such bottom plate 33 is presented in FIGS. 3A and 3B as spotted hatching while the grounding elements 23 are presented as dashed. There may be one, two, three or four grounding elements, for example two at the both sides of the housing at one end of the housing. The bottom plate 33 may be used for example if the circuit board is thin and/or flexible and needs support. If the circuit board is rigid, it may replace the bottom plate. The thickness of the rigid circuit board may be in the range of 0.4-2 mm, for example in the range of 0.6-1.0 mm.

The biometric monitor generally includes one or more processors, memory, one or more biometric sensors, an interface, and optionally a display arranged to present information, operatively connected together. The biometric monitor naturally contains a power source, for example a battery and/or a solar cell. The one or more processor(s) is/are configured to process the biometric information which is measured by the one or more sensors, to determine an output from the measurement. The one or more processor(s) is/are usually comprised in a control unit or in means for controlling the biometric monitor. The determined information may be outputted to a display, or the information may be sent to an external device wirelessly connected to the biometric monitor, for example by using Bluetooth, WiFi, cellular or any other suitable wireless technology. In such case the biometric monitor contains means for wireless communication, such as a transmitter and a receiver configured to communicate with the external device. One or more of the one or more processors, the memory, one or more biometric sensors, the interface, the transmitter/receiver and the display arranged to present information are usually implemented as one or more electronic circuit boards and/or modules. Examples of these parts can be seen in the explosion views of FIGS. 2A and 2B. The device may also contain audio means for outputting and/or inputting sound, for example as a part of the user interface.

The display may use one or more of any of the suitable display technologies including LED, LCD, AMOLED, E-Ink, Sharp display technology, graphical display, and other suitable display technologies. This display may be used to present data acquired or stored locally on the device or data acquired remotely from other devices or Internet services.

The external device may be a mobile terminal, for example a handheld device such as a mobile phone, a phablet or a tablet, or a computer, for example as a portable computer or any other computer, or any other suitable external device. The information may be processed and/or displayed in the external device, for example the information may be collected, saved, processed and analyzed. Other types of information may also be combined with the measured biometric information, such as geographic information for example obtained from a GPS system in the device itself or in the external device, time information, temperature information, and the like. The other information may be measured using the same device or the other information may be obtained from another source or device, such as the external device. The combined information may be processed to a presentable form, for example to present statistical information as graphs or tables.

The interface may comprise a user interface for indicating the state of one or more data types measured and/or analyzed. The user interface may also include one or more physical buttons and/or a touch sensitive screen as means for controlling the device and/or interacting with it, or a combination thereof. The interface may also comprise means for communicating with an external device by using wireless technology. The interface may also comprise means for presenting information on a display. FIGS. 2A and 2B show examples of physical buttons between the pivots on the sides of the housing. The buttons contain a spring for enabling non-locking key functionality. In this example there is a further side plate 38 between the spacer elements 12, 13, 14, 15, wherein this side plate 38 contains a hole for receiving the button 37 and has the same thickness as the spacer elements 12, 13, 14, 15. This enables providing the button on the same level as the spacer elements, and the button may be pressed inwards. Therefore the button does not extend from the side of the monitor and it also does not reserve space inside the housing.

One embodiment provides a strap for connecting to a housing of a portable biometric monitor, said strap comprising a first end and a second end, wherein the strap includes spacer elements having a first end and a second end, the strap is arranged to be connected from its two sides at the first end and from its two sides at the second end to two sides at the first end of the housing and to two sides at the second end of the housing via pivots connected to said spacer elements to allow pivoted movement of the housing. The distance of the pivot locations between the first end of the housing and the second end of the housing may be in the range of 10-30 mm, for example in the range of 20-30 mm. The distance of the pivot locations between the first end of the housing and the second end of the housing refers to the distance at the same side of the housing.

Figure 4A:
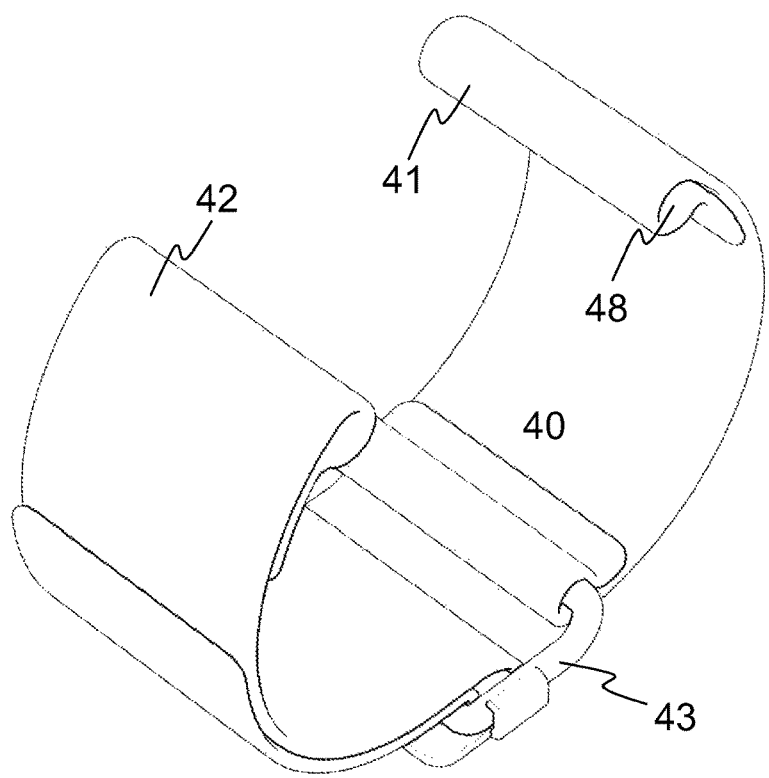
FIG. 4A shows a general view of a strap with a buckle.
Figure 4B:
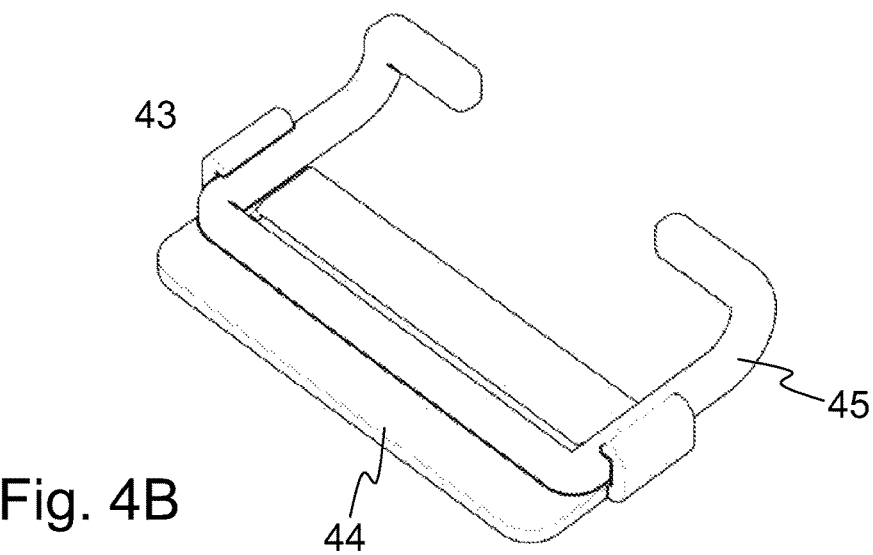
FIG. 4B shows the buckle
Figure 5A:
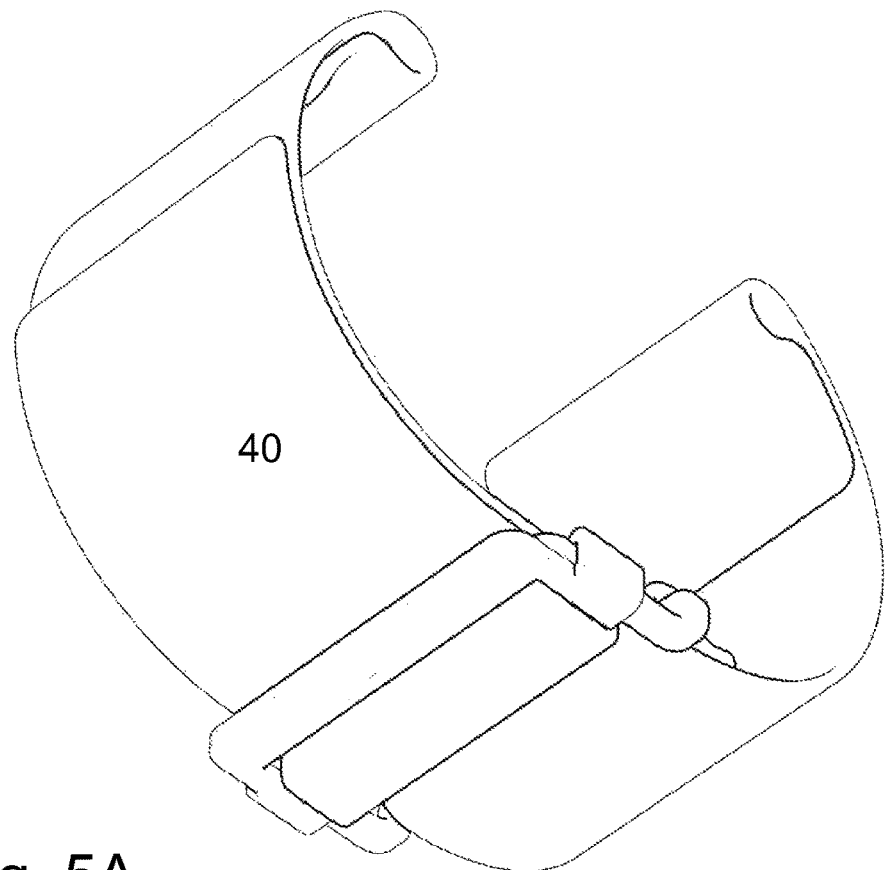
FIG. 5A shows a general view of a strap with a buckle.
Figure 5B:
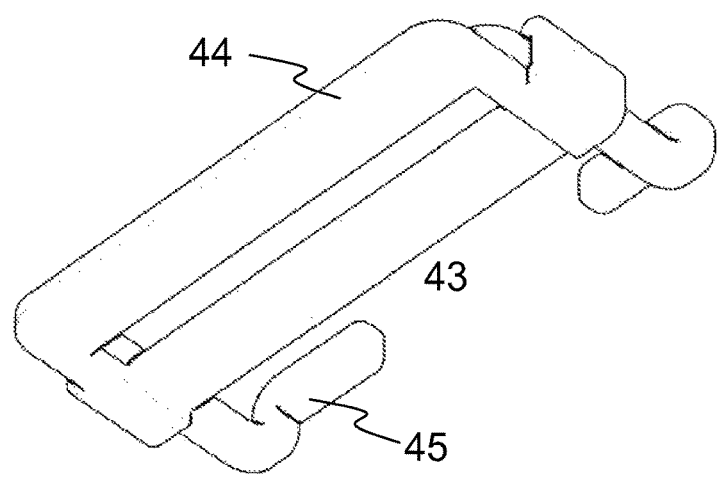
FIG. 5B shows the buckle

FIGS. 4A and 5A shows a two-part strap wherein the parts are connected by a buckle 43, which is shown in more detail in FIGS. 4B and 5B. One part of the strap enters the buckle, which is arranged to receive said strap, the strap forming a loop therein and exits the buckle 43 back to the opposite direction. The other part of the strap contains a loop for receiving the base member 45 of the buckle 43. The basic structure of a buckle 43 is shown in FIGS. 4B and 5B, the buckle having a movable member 44 and a base member 45 forming a window for the strap 40. Pulling the strap is arranged to close the window by moving the movable member 44. In such construction the part of the strap which is in self-contact, i.e. entering and exiting the buckle, may extend and/or contract due to the user body movement. This results in loosening of the strap, or in some cases even unwanted tightening of the strap.

Figure 6A:
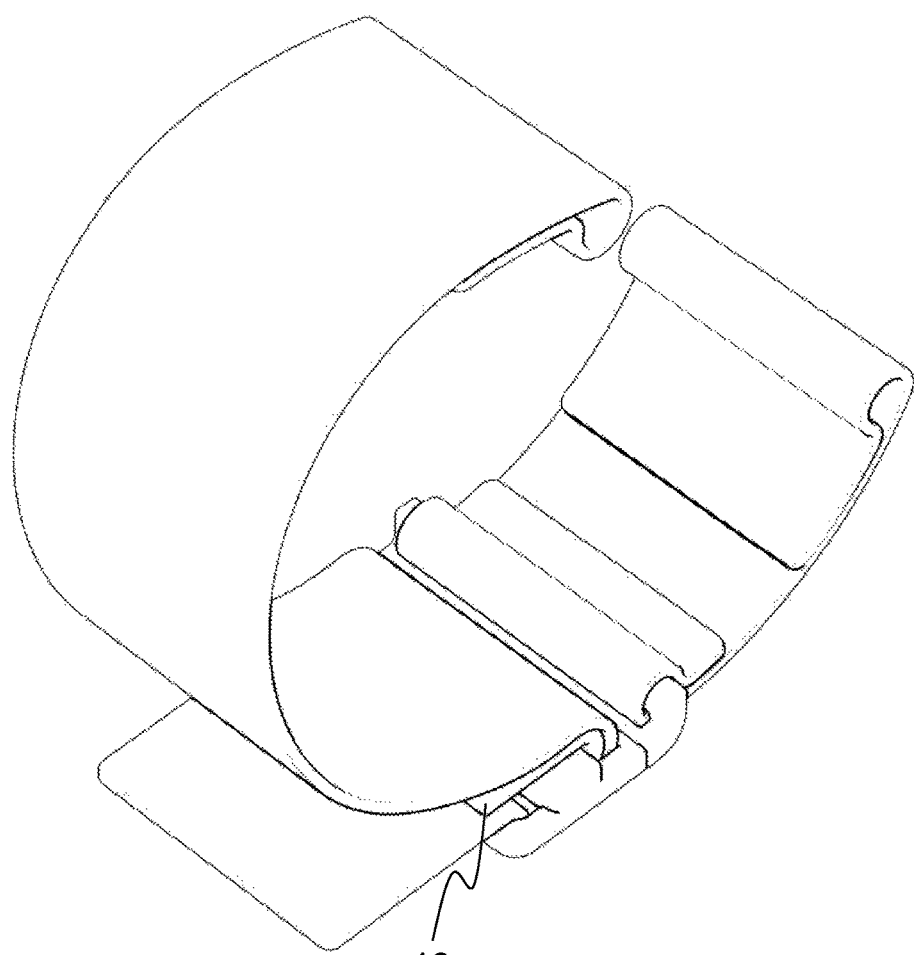
FIG. 6A shows a general view of a strap with a buckle.
Figure 6B:
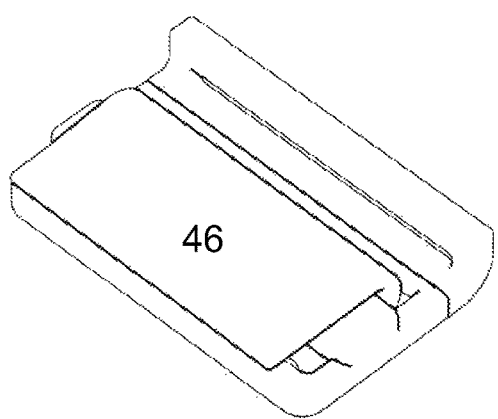
FIG. 6B shows a buckle with an extension part between the strap parts
Figure 7A:
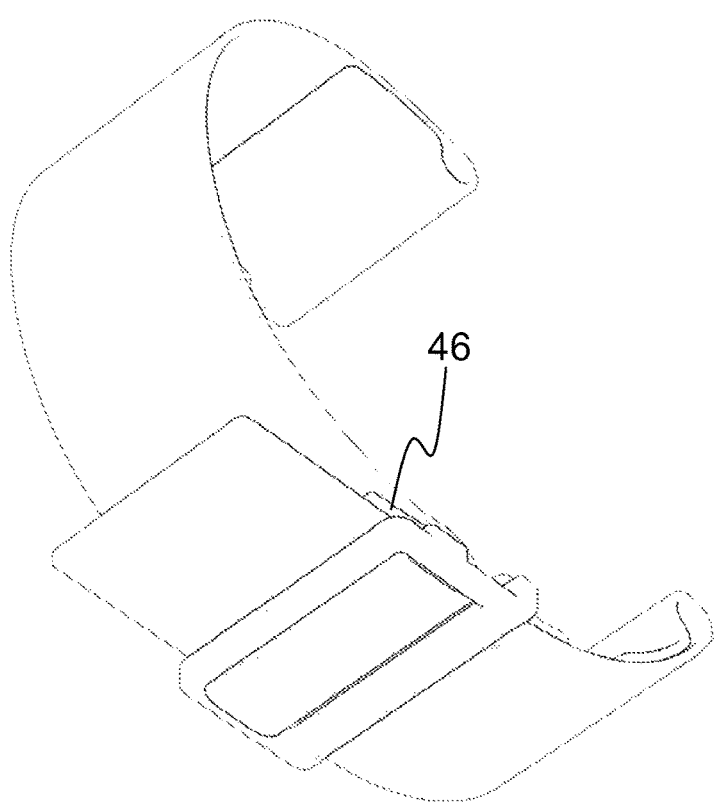
FIG. 7A shows a general view of a strap with a buckle.
Figure 7B:
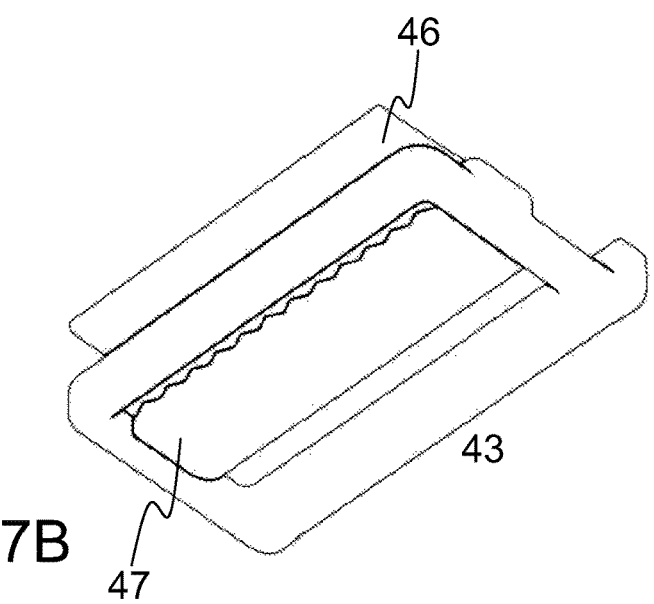
FIG. 7B shows a buckle with a first extension part and a second extension part

In one embodiment the strap of a portable biometric monitor comprises a buckle 43, wherein a movable member 44 and a base member 45 are arranged to form a window for the strap 40, and pulling the strap is arranged to close the window by moving the movable member 44. The movable member may have an extension that allows for controlled loosening of the buckle 43 by pressing from the side. The movable member has an intermediate part 46 between the two portions of the strap 40 arranged to enter and exit the buckle 43 to prevent the strap 40 from being moved through the window by friction when the flexible strap 40 is extending and contracting due to user body movement. This facilitates maintaining the desired tightness of the strap even in active use thus enhancing the stability of the biometric monitor on the user by maintaining the desired contact. FIG. 6A shows a two-part strap having a first strap part and a second strap part, wherein the parts are connected by a buckle 43 having the intermediate part 46 between the two portions of the strap 40. FIG. 7A shows the buckle 43 with the intermediate part 46 from another angle. FIG. 7B shows the other end 47 of the movable member, which in this example contains a serrated part for contacting the strap.

In one example the strap further comprises a mechanical indicator configured to indicate the tightness of a strap of a portable biometric monitor. Said indicator further facilitates maintaining the desired tightness of the strap, and enables the adjustment of the strap tightness according to different activities and/or time of the day.

In one example the strap is a stretchable strap comprising a non-stretchable sliding part built-in in the stretchable strap, wherein the stretchable strap comprises a section through which the indicator on the non-stretchable sliding part is visible. In one example the strap is a stretchable strap comprising a stretchable sliding part built-in in the stretchable strap, the stretchable sliding part being less stretchable than the stretchable strap, wherein the stretchable strap comprises a section through which the indicator on the stretchable sliding part is visible. In one example the indicator is provided by knitting the strap such that it provides a meter showing the level of tightness of the strap.

In one example the mechanical indicator is arranged into a spacer element or link part connected to a main body of the portable biometric monitor and to which the strap is attached. In one example the spacer element comprises a window in which the mechanical indicator is movable to indicate the tightness of the strap. In one example the spacer element comprises a rotating part to which the strap is attached. The indicator is attached to the rotating part such that when the rotating part rotates, the indicator moves in the window. In one example the spacer element comprises a sliding part to which the strap is attached. The indicator is attached to the sliding part such that when the sliding part moves, the indicator moves in the window.

Figure 8:
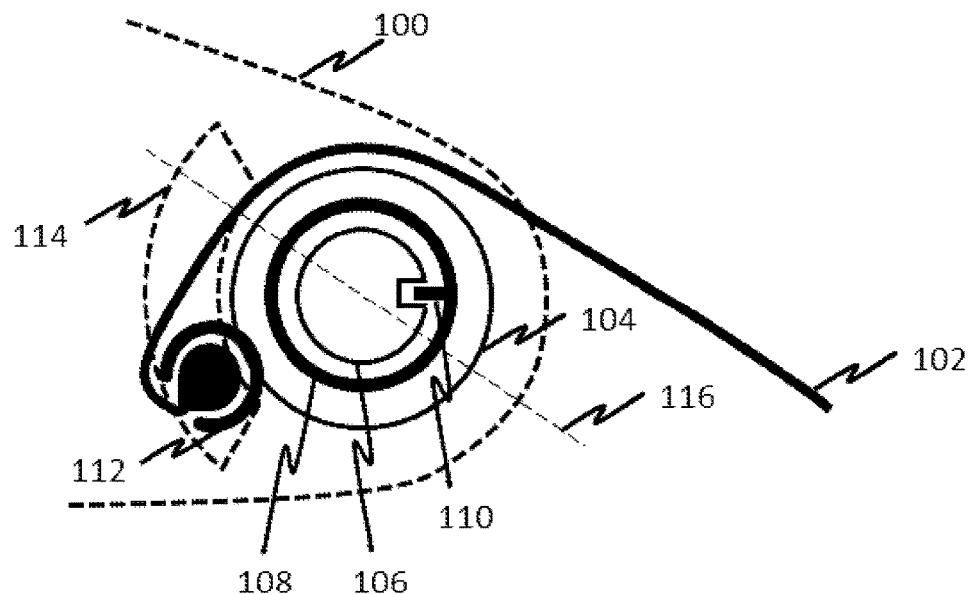
FIG. 8 shows an arrangement comprising a mechanical indicator configured to indicate tightness of a strap

A spacer element 100 of the portable biometric monitor provides an attachment point to a strap 102. The spacer element 100 may be removably attachable to a main body (not shown) of the portable biometric monitor, or alternatively, the spacer element 100 may be an integral part of the main body. The spacer element 100 includes a fixed axle 106. A sliding part and a resilient member, for example a spring 108, are arranged around the fixed axle 104. Instead of the spring, any other resilient member may be used. A rotation blocker 110 is attached to the sliding part 108 in order to prevent the sliding part 108 to rotate around the fixed axle 106. A rotating non-sliding part 104 is arranged as an outmost element and the strap 102 is in contact with the rotating non-sliding part 104 in a section of its circumference, as illustrated in FIG. 8. Reference number 112 indicates that the strap 102 is attached to the rotating non-sliding part 104. The spacer element 100 includes a window 114, for example a hole, in which an indicator is movable and the location of the indicator in the hole 114 depends on the tightness of the strap 102 when a user of the portable biometric monitor fastens the device, for example, around his wrist.

In one example the indicator is attached to the rotating non-sliding part 104 and thus it moves when the rotating non-sliding part 104 rotates. The indicator may be a peg which moves in the window 114. In another example the indicator is a plate movable in the window 114 and it comprises a scale. A pointer has been arranged in the spacer element 100. When the plate moves as a result of pulling the strap, the pointer points to a certain point in the scale on the plate indicating the tightness of the strap.

As illustrated in FIG. 8, the hole 114 may take a form of a slot which is radially arranged in relation to the fixed axle 106. Reference number 116 refers to a cross-section which is illustrated in more detail in FIG. 9.

In one example the window 114 is a hole in the spacer element. In another embodiment, the spacer element 100 comprises transparent section through which the indicator can be seen. For example, the spacer element 100 may be partly or wholly made of plastic and it may be partly or wholly transparent.

Figure 9:
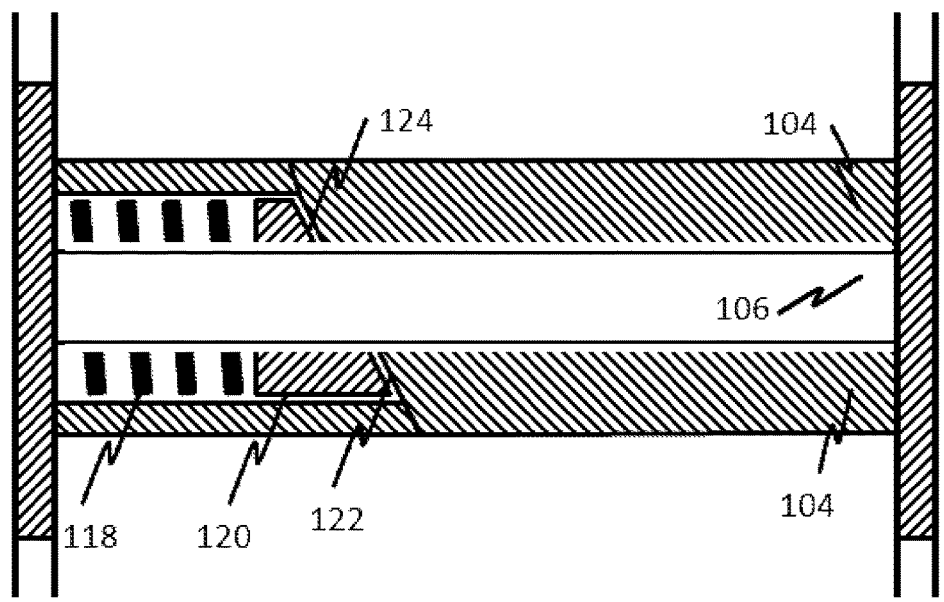
FIG. 9 shows discloses a cross-section view of the arrangement of FIG. 8

FIG. 9 discloses a cross-section view of the arrangement of FIG. 8. As illustrated in FIG. 9 the rotating non-sliding part 104 partially directly surrounds the fixed axle 106 and is arranged to be rotatable about the fixed axle 106. The remaining part of the fixed axle 106 not directly surrounded by the rotating non-sliding part 104 is occupied by a spring 118 and a non-rotating sliding part 120.

When the strap 102 is pulled the rotating non-sliding part 104 rotates around the fixed axle 106. An inclined surface 122 of the rotating non-sliding part 104 faces towards an inclined surface 124 of the sliding non-rotating part 120. When the rotating non-sliding part 104 rotates it presses the sliding non-rotating part 120, and due to the inclined surfaces 122 and 124, the sliding non-rotating part 120 moves and compresses the spring 118. Although not illustrated in FIG. 9, this action also moves the indicator in the hole 114. When the pulling stops and the tightness of the strap 102 is reduced, the spring 118 presses the sliding non-rotating part 120 and the sliding non-rotating part 120 generates a rotating force for the rotating non-sliding part 104 and thus the rotating non-sliding part 104 turns to its relaxed position.

Figure 10:
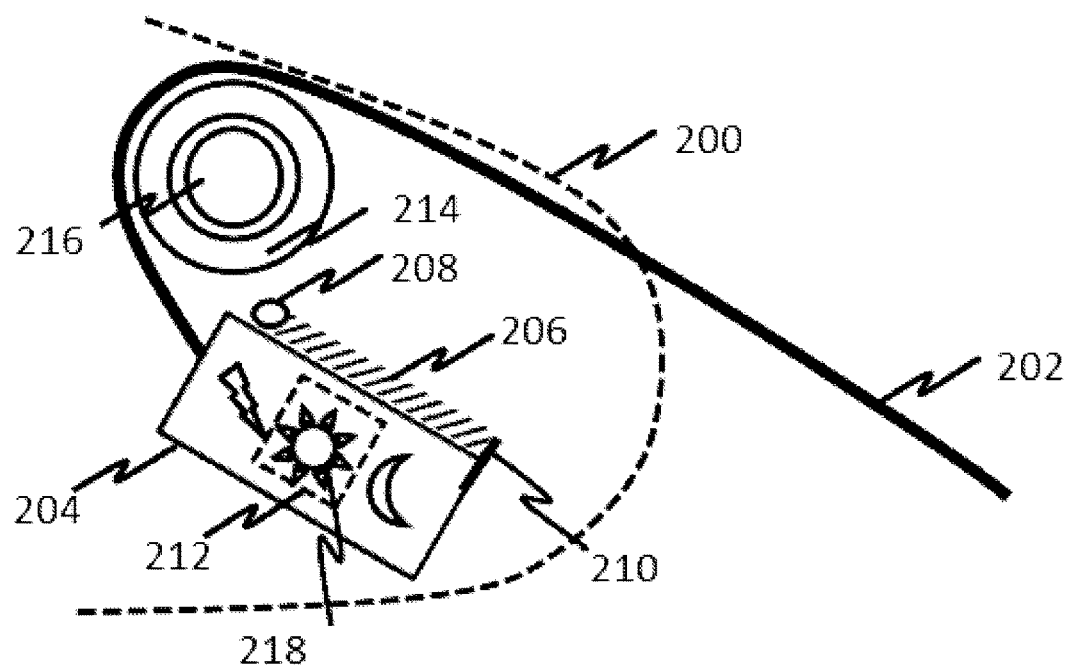
FIG. 10 shows an arrangement comprising a mechanical indicator configured to indicate tightness of a strap

FIG. 10 discloses an arrangement comprising a mechanical indicator configured to indicate tightness of a strap 202 of a portable biometric monitor according to one embodiment of the invention. Whereas FIG. 8 disclosed a turning force indicator FIG. 10 discloses a sliding force indicator. A spacer element 200 of the portable biometric monitor provides an attachment point to the strap 202. The spacer element 200 may be removably attachable to a main body (not shown) of the portable biometric monitor or alternatively the spacer element 200 may be an integral part of the main body. The spacer element 200 includes a fixed axle or pivot 216. A rotating part 214 is arranged to be rotatably attached to the fixed axle 216. The strap 202 is arranged to be partially in contact with the rotating part 214 on the circumference of the rotating part 214, as disclosed in FIG. 10. A sliding part 204 is arranged in the spacer element 200 and the strap 202 is attached to the sliding part 204.

A first spring blocker 208 is arranged in the spacer element 200 and a second spring blocker is arranged in the sliding part 204. A spring 206 is arranged between the first spring blocker 208 and the second spring blocker 210. In one example the sliding part 204 comprises guiders which keep the sliding part 204 on its sliding track in the spacer element 200. When the strap 202 is pulled, the sliding part 204 moves and the spring 206 compresses. Instead of the spring 206, any other resilient member may be used. The spacer element 200 also includes a window 212 through which an indicator 218 in the sliding part 204 or attached to the sliding part 204 can be seen. In one example the window 212 is a hole in the spacer element 200. In another example the spacer element 200 comprises a transparent section through which the indicator in the sliding part 204 or attached to the sliding part 204 can be seen. For example, the spacer element 200 may be partly or wholly made of plastic. Furthermore, it may be partly or wholly transparent.

As an example of the indicator, FIG. 10 discloses that the sliding part includes three patterns for indicating the tightness of the strap 202. Only one pattern can be seen in whole at a time through the window 212 in the spacer element 200. It is evident that FIG. 10 discloses only one example of a possible indicator. In another example an elongated slot may be arranged in the spacer element 200 and an indicator attached to the sliding part 204 moves in the elongated slot and indicates the current tightness of the strap 202.

Figure 11:
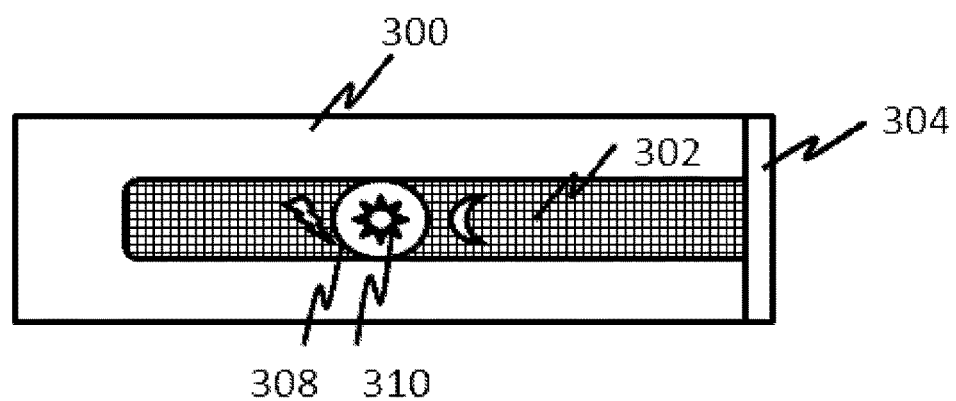
FIG. 11 shows an example of a strap

FIG. 11 discloses a strap 300 for a portable biometric monitor according to one embodiment of the invention. The strap 300 and a sliding part 302 are attached to a fixation part 304 via which they can be attached to a portable biometric monitor body part. In the example disclosed in FIG. 11, an indicator 310 indicating tightness of the strap 300 is included in the strap 300 itself. The strap 300 is stretchable. A sliding part 302 that is not stretchable, or has different stretching properties than the stretchable strap 300, is built-in in the stretchable strap 300. The sliding part 302 is configured in the stretchable strap 300 so that when the strap 300 stretches, the sliding part 302 remains unstretched. In other words, to achieve this functionality a cavity may be arranged in the strap 300 for the sliding part so that the sliding part 302 does not move when the strap 300 is stretched. The sliding part 302 has been equipped with one or more patterns, i.e. indicators 310, to indicate the tightness of the strap. When the strap is pulled (i.e. when a user fastens the portable biometric monitor comprising the strap, for example, onto his wrist and tightens the strap), the strap stretches and an indicator hole 308 moves in relation to the non-stretchable sliding part 302. A pattern indicating the tightness of the strap 300 is then visible via the hole 308.

Figure 12:
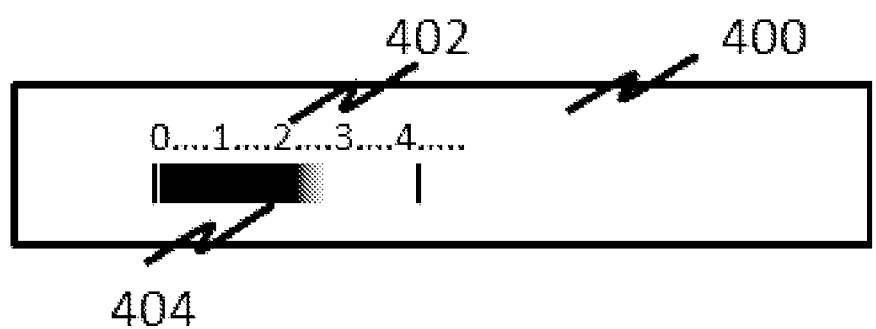
FIG. 12 shows an example of a strap

In another example of FIG. 11, the strap 300 is a stretchable strap comprising a sliding part 302 built-in in the stretchable strap 300. The sliding part 302, however, is stretchable but less stretchable than the stretchable strap 300. In other words, when the strap 300 is pulled (i.e. when a user fastens the portable biometric monitor comprising the strap, for example, onto his wrist and tightens the strap), the strap 300 stretches, and at the same time, also the sliding part 302 stretches but less than the strap 300. An indicator hole 308 arranged in the strap 300 moves in relation to the sliding part 302, and an indicator 310 is visible through the indicator hole 308. FIG. 12 discloses a strap 400 for a portable biometric monitor according to one example. As in the example of FIG. 11, the strap 400 of the example of FIG. 12 is stretchable.

The strap 400 has been specially configured so that when the strap 400 is stretched, it shows a meter 404 showing the tension level of the strap 400. The strap 400 may include a numerical scale 402 or some other type of a scale or pattern to provide information about the tension/tightness of the strap 400. The meter 404 can be achieved, for example, by a special knitting of the strap 400 wholly or partially. When the strap 400 is stretched, the special knitting enables the meter 404 to be seen indicating the tension/tightness of the strap 400.

A benefit of the examples disclosed in FIGS. 8-12 is that the guided adjustment of tightness of the strap enables the use of the portable biometric monitor in various operating situations. Moreover, the solution enables optimal strap tightness and avoids excessive loosening or tightening. Furthermore, the disclosed solution also takes into account physiological variations between individuals. Furthermore, the examples disclosed in FIGS. 8-12 are also advantageous for example when measuring pulse with biometric monitors that use optical pulse measurement techniques since undesired movements of the device may cause disturbances in the measurements. With the disclosed examples it is possible to ensure optimal strap tightness of the strap.

Next the embodiments will be described with a reference to an exemplary implementation of a biometric monitor and a wrist strap.

Examples

The FIGS. 1A and 1B illustrate an exemplary embodiment of a biometric monitor 10 having an optical sensor at the bottom of the housing 20. The housing 20 has a length d of about 32 mm, and a width c of about 26 mm (the spacer elements are not included). The distance a between the pivot locations between the first end of the housing and the second end of the housing is about 21.5 mm. The distance between the center of the pivots 17, 19 in the first end 24 and in the second end 25 of the spacer elements 12, 13, 14, 15 is about 10 mm, the length b of the spacer elements being about 17 mm. The distance e of a pivot 17 center from an end 21 of the housing 20 is about 5 mm.

In this example the spacer elements and the pivots are made of steel, and the housing 20 and the axles 11 are made of plastics. The side plate 38 between the spacer elements and the buttons 38 embedded therein are made of steel. The side plate has curved ends for receiving the corresponding ends 25 of the spacer elements 12, 13, 14, 15. The side plate is attached by pegs to a metallic connecting part 39 which also has protruding parts having holes for receiving the two pivots on the same side of the monitor (FIG. 3B). This part anchors most of the metallic parts enabling the housing to be made of plastics.

The assembly of the monitor is illustrated in FIGS. 2A and 2B. On the bottom there is a housing 20 having apertures 30 for receiving the parts of the optical sensor 31. The parts of the optical sensor are attached to a bottom plate 33. A gasket or sealing plate 32 prevents a leakage of the light inside the device. The metallic grounding members 23 are attached to the bottom plate 33 to enable the grounding of the system. The spring-like grounding parts 23 are arranged to be pressed against the inner ends of the pivots 16, 17, to enable electrical contact for grounding, as seen in the FIGS. 3A and 3B. Above the bottom plate there is a battery 34 and a board 26 containing the electronics. The battery is connected to charging clips 27 at the bottom of the monitor. The display 35 is located on top of the electronics module and it is covered by a partly transparent display cover 36, which is the topmost part of the assembly. In the illustrated example there is also a GPS antenna 28 located near the display 35 below the cover 36.

There is one button 37 at both sides of the monitor. The buttons 37 include a spring and a metallic lockwasher as fastening means inside the housing 20. The pivots are fastened using similar lockwashers inside the housing.

The straps 40 illustrated in FIGS. 4A, 5A, 6A and 7A are made of two stretchable canvas parts, which are connected by a buckle 43. The buckle has a movable member 44 and a base member 45 which form a window for the strap. The movable member has a first extension 47 that allows for controlled loosening of the buckle 43 by pressing from the side. The movable member has an intermediate part as a second extension 46 between the two portions of the strap entering and exiting the buckle to prevent the strap from being moved through the window by friction when the flexible strap is extending and contracting due to user body movement.

The invention claimed is:

1. A portable biometric monitor assembly for obtaining a photoplethysmogram (PPG), the assembly comprising:
    an optical sensor;
    a housing for said portable biometric monitor; and
    a strap configured to be connected to the housing for attaching the portable biometric monitor to a user, the strap comprising a first end and a second end, the first end of the strap being configured to be connected to a first set of spacer elements and the second end of the strap being configured to be connected to a second set of spacer elements:
        wherein the first set of spacer elements at the first end of the strap includes a first spacer element on a first side of the strap and a second spacer element on a second side of the strap; and
        the second set of spacer elements at the second end of the strap includes a first spacer element on the first side of the strap and a second spacer element on the second side of the strap;
        wherein each spacer element is independently movable, and each spacer element has a first end and a second end,
    the strap being connected from its two sides at the first end and from its two sides at the second end to two sides at the first end of the housing and to two sides at the second end of the housing via pivots connected to said spacer elements at the sides of the housing to allow pivoted movement of the housing, wherein
    a distance (a) of pivot locations between the first end of the housing and the second end of the housing is in a range of 10-30 mm.

2. The portable biometric monitor of claim 1, wherein the distance (a) of the pivot locations between the first end of the housing and the second end of the housing is in the range of 20-30 mm.

3. The portable biometric monitor of claim 1, wherein the pivots are connected to the housing at locations which are at a distance (e) in the range of 3-10 mm from the end of the housing.

4. The portable biometric monitor of claim 1, wherein the pivots are connected to the housing at locations which are at a distance (e) in the range of 4-6 mm from the ends of the housing.

5. The portable biometric monitor of claim 1, wherein the pivots on the two sides of the housing are separate pivots not penetrating through the whole housing.

6. The portable biometric monitor of claim 1, wherein the spacer elements are freely movable.

7. The portable biometric monitor of claim 1, wherein the pivot is non-movable at the housing side.

8. The portable biometric monitor of claim 1, wherein the strap is a wrist strap.

9. The portable biometric monitor of claim 1, wherein the spacer elements have a length (b) in the range of 10-20 mm.

10. The portable biometric monitor of claim 1, wherein the spacer elements have a length (b) in the range of 15-18 mm.

11. The portable biometric monitor of claim 1, wherein the biometric sensor is located on the skin side of the monitor.

12. The portable biometric monitor of claim 1, wherein the optical sensor is located on the skin side of the monitor.

13. The portable biometric monitor of claim 1, further comprising at least one sensor selected from a temperature sensor, a potential sensor, a sound or an ultrasound sensor, an impedance sensor, a galvanic skin response sensor (GSR), an EKG sensor, an EMG sensor, and a wavelength sensor.

14. The portable biometric monitor of claim 1, wherein the biometric monitor is a heart rate monitor.

15. The portable biometric monitor of claim 1, wherein said pivots and spacer elements are made of metal.

16. The portable biometric monitor of claim 1, wherein the biometric monitor is grounded to a metallic pivot from inside the housing.

17. The portable biometric monitor of claim 16, wherein the biometric monitor is grounded to the metallic pivot via a spring member.

18. The portable biometric monitor of claim 1, wherein the housing is water-resistant.

19. The portable biometric monitor of claim 1, wherein the strap comprises a buckle, wherein a movable member and a base member are arranged to form a window for the strap, pulling the strap is arranged to close the window by moving the movable member, the movable member having an intermediate part between two portions of the strap arranged to enter and exit the buckle to prevent the strap from being moved through the window by friction when the flexible strap is extending and contracting due to user body movement.

20. The portable biometric monitor of claim 1, wherein:
    a first pivot of the pivots at the first end of the strap connects the first end of the strap to the first spacer element on the first side of the first end of the strap and the second spacer element on the second side of the first end of the strap; and
    a first pivot of the pivots at the second end of the strap connects the second end of the strap to the first spacer element on the second side of the second end of the strap and the second spacer element on the second side of the second end of the strap.

21. The portable biometric monitor of claim 20, wherein:
    a second pivot of the pivots at the first end of the strap connects a first side at the first end of the housing to the first spacer element at the first side of the first end of the strap and a second side of the first end of the housing to the second spacer element at the second side of the first end of the strap; and a second pivot of the pivots at the second end of the strap connects a first side at the second end of the housing to the first spacer element at the first side of the second end of the strap and a second side of the second end of the housing to the second spacer element at the second side of the second end of the strap.

22. The portable biometric monitor of claim 1, wherein each spacer element is movable to form an angle with the housing independently.

23. The portable biometric monitor of claim 1, wherein each spacer element is movable to form a different angle with the housing.

* * * * *